US008636646B2

(12) United States Patent
Daniel (10) Patent No.: US 8,636,646 B2
(45) Date of Patent: *Jan. 28, 2014

(54) PENILE IMPLANT WITH DILATANT LIQUID (75) Inventor: Geoffrey A. Daniel, Crystal, MN (US)

(73) Assignee: Coloplast A/S, Humlebaek (DK)

( * ) Notice: Subject to any disclaimer, the term of this patent is extended or adjusted under 35 U.S.C. 154(b) by 0 days.

This patent is subject to a terminal disclaimer.

(21) Appl. No.: 13/403,372

(22) Filed: Feb. 23, 2012

(65) Prior Publication Data

US 2012/0184807 A1    Jul. 19, 2012

Related U.S. Application Data (63) Continuation of application No. 13/225,581, filed on Sep. 6, 2011, now Pat. No. 8,147,400, which is a continuation of application No. 13/008,027, filed on Jan. 18, 2011, now Pat. No. 8,419,612.

(30) Foreign Application Priority Data

Jan. 17, 2011    (DK) .................................. 2011 70019

(51) Int. Cl.
*A61F 5/00*    (2006.01)

(52) U.S. Cl.
USPC ............................................................. 600/40

(58) Field of Classification Search
USPC .............................. 600/38–41; 128/897–898
See application file for complete search history.

(56) References Cited

U.S. PATENT DOCUMENTS

| 3,601,923 | A | * | 8/1971 | Rosenberg | .................... 446/267 |
| 8,147,400 | B1 | * | 4/2012 | Daniel | ............................ 600/40 |
| 2012/0136205 | A1 | * | 5/2012 | Aguilera Galeote | ............ 600/38 |

FOREIGN PATENT DOCUMENTS

| WO | 2007073556 A2 | 6/2007 |
| WO | 2008107716 A1 | 9/2008 |

* cited by examiner

*Primary Examiner* — Samuel Gilbert
(74) *Attorney, Agent, or Firm* — Coloplast Corp., Coloplast A/S; Nick Baumann (57) ABSTRACT

A penile prosthetic assembly includes a penile implant containing a dilatant liquid and a reservoir connectable with the penile implant. Fluid transferred from the reservoir into the penile implant imposes a shear on the dilatant liquid to increase viscosity in the dilatant liquid and harden the penile implant.

5 Claims, 11 Drawing Sheets

“PENILE IMPLANT WITH DILATANT LIQUID

BACKGROUND

An implanted penile prosthetic is effective in relieving erectile dysfunction in men.

A penile prosthetic typically includes one or more cylinders that are implanted in the corpora cavernosa of the penis, a liquid reservoir implanted in the abdomen that communicates with the cylinder(s), and a pump, often located in the scrotum, that is employed to move liquid from the liquid reservoir into the cylinder(s).

In a typical application, the user squeezes a bulb of the pump multiple times to incrementally draw liquid out of the liquid reservoir, into the bulb, and eventually into the cylinders. The repeated squeezing of the bulb moves the liquid from the reservoir into the cylinders, which incrementally deflates the reservoir and incrementally inflates the cylinder (s) to eventually provide the user with an erect penis. The user may return the penis to its flaccid state by selectively transferring the liquid from the cylinder(s) back into the reservoir.

The above-described penile prosthetics have proven effective in relieving erectile dysfunction in men. However, men have expressed a continuing desire for more spontaneous, efficient, and effective penile prostheses.

SUMMARY

One aspect provides a body implantable penile prosthetic assembly including a penile implant and a reservoir. The penile implant includes a first bladder and a second bladder, where the second bladder contains a dilatant liquid. The reservoir is connectable with the first bladder of the penile implant. The fluid transferred from the reservoir into the first bladder of the penile implant imposes a shear on the dilatant liquid in the second bladder of the penile implant to increase viscosity in the dilatant liquid and harden the penile implant.

One aspect provides a method treating erectile dysfunction. The method includes implanting a penile implant including a first bladder and a second bladder, the second bladder filled with a liquid having a rest viscosity. The method additionally includes increasing a pressure in the first bladder of the penile implant from a first pressure to a second pressure, and increasing a viscosity in the liquid from the rest viscosity to a second viscosity greater than the rest viscosity. The method further includes maintaining the first bladder of the penile implant at the second pressure and the liquid in the second bladder at the second viscosity.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

DETAILED DESCRIPTION

In the following Detailed Description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the appended claims.

It is to be understood that the features of the various exemplary embodiments described herein may be combined with each other, unless specifically noted otherwise.

The term "proximal" as employed in this application means that the referenced part is situated next to or near the point of attachment or origin or a central point: as located toward a center of the human body. The term "distal" as employed in this application means that the referenced part is situated away from the point of attachment or origin or the central point: as located away from the center of the human body. A distal end is the furthest endmost location of a distal portion of a thing being described, whereas a proximal end is the nearest endmost location of a proximal portion of the thing being described. For example, the glans penis is located distal, and of the crus of the penis is located proximal relative to the male body such that a distal end of a corpora cavernosum of the patient extends about midway into the glans penis.

A dilatant liquid is a fluid having a viscosity that increases as shear is applied to the dilatant liquid. A dilatant liquid will thus "harden" or become thicker when shear stress is applied to the dilatant liquid, and in some cases this hardening is nearly instantaneous in response to the applied stress. The dilatant liquid will remain hardened in the thickened state until the shear stress is removed, which provides the dilatant liquid with reversible thickening properties. For example, a dilatant liquid with an "at-rest" viscosity will thicken/harden to a higher viscosity when a shear stress of 10 psi is applied to the dilatant liquid; when the shear stress is reduced, the viscosity will be reduced, and at zero applied shear stress the dilatant liquid will return to the lower at-rest viscosity.

In contrast, one definition of a rheopexic fluid is a fluid having a viscosity that increases with a rate of change of shear applied to the rheopexic fluid. A rheopexic fluid will thus "harden" or become thicker in the presence of changing shear stress applied to the rheopexic fluid. One definition of a rheopexic fluid is a fluid having a viscosity that is time-dependent upon application of stress. This kind of rheopexic fluid requires that the stress be applied for a significant portion of time, from several seconds to several minutes depending on formulation, for any change in viscosity to occur. The rheopexic fluid will return to its initial lower viscosity state whenever the applied stimulation ceases. For example, a rheopexic fluid with a constant shear stress of 10 psi will not respond with an increase in viscosity since a rheopexic fluid responds to the rate of change in the shear stress. In other words, a rheopexic fluid requires continuous stimulation (or a shear stress that is continually changing) in order to exhibit the hardened state. A rheopexic fluid thickens in response to changing shear stress such that even if the shear stress is relatively high at 10 psi the rheopexic fluid will not thicken since the constant shear stress of 10 psi has a rate of change of shear that is zero.

Embodiments provide a penile implant having a first bladder and a second bladder, where the second bladder contains a dilatant liquid. A reservoir is connected with the first bladder of the penile implant. When fluid is transferred from the reservoir into the first bladder, a shear is imposed on the dilatant liquid in the second bladder. The shear on the dilatant liquid increases the viscosity of the liquid in the second bladder resulting in a hardening of the penile implant. Since a portion of the penile implant is filled with dilatant liquid, the reservoir can be configured as a liquid-sparing reservoir that is smaller than a typical reservoir and more comfortable to implant into the abdomen of the patient. To this end, the prosthetic device is more comfortable for the patient. In some embodiments, the prosthetic device includes a pump for moving liquid from the reservoir into the first bladder. The liquid-sparing reservoir configures the prosthetic device to operate with fewer squeezes of the pump, which improves comfort and convenience for the user.

Embodiments provide a penile implant having a first bladder and a second bladder, where the second bladder contains a dilatant liquid. In an at-rest state, the dilatant liquid will configure the implant to be flaccid. When the user desires an erection, the implant is configured to harden to an erect state in response to shear applied to the dilatant liquid. For example, an erection is achievable by employing a pump to increase the pressure in the first bladder of the implant to apply shear to the dilatant liquid, perhaps in expectation of coitus. In this regard, the user can apply the shear stress to the implant and harden it to the erect state prior to having relations, and upon cessation of the pumping of the liquid into the first bladder, the implant will maintain in the hardened erect state until the use selectively relieves the pressure in the first bladder.

Figure 1:
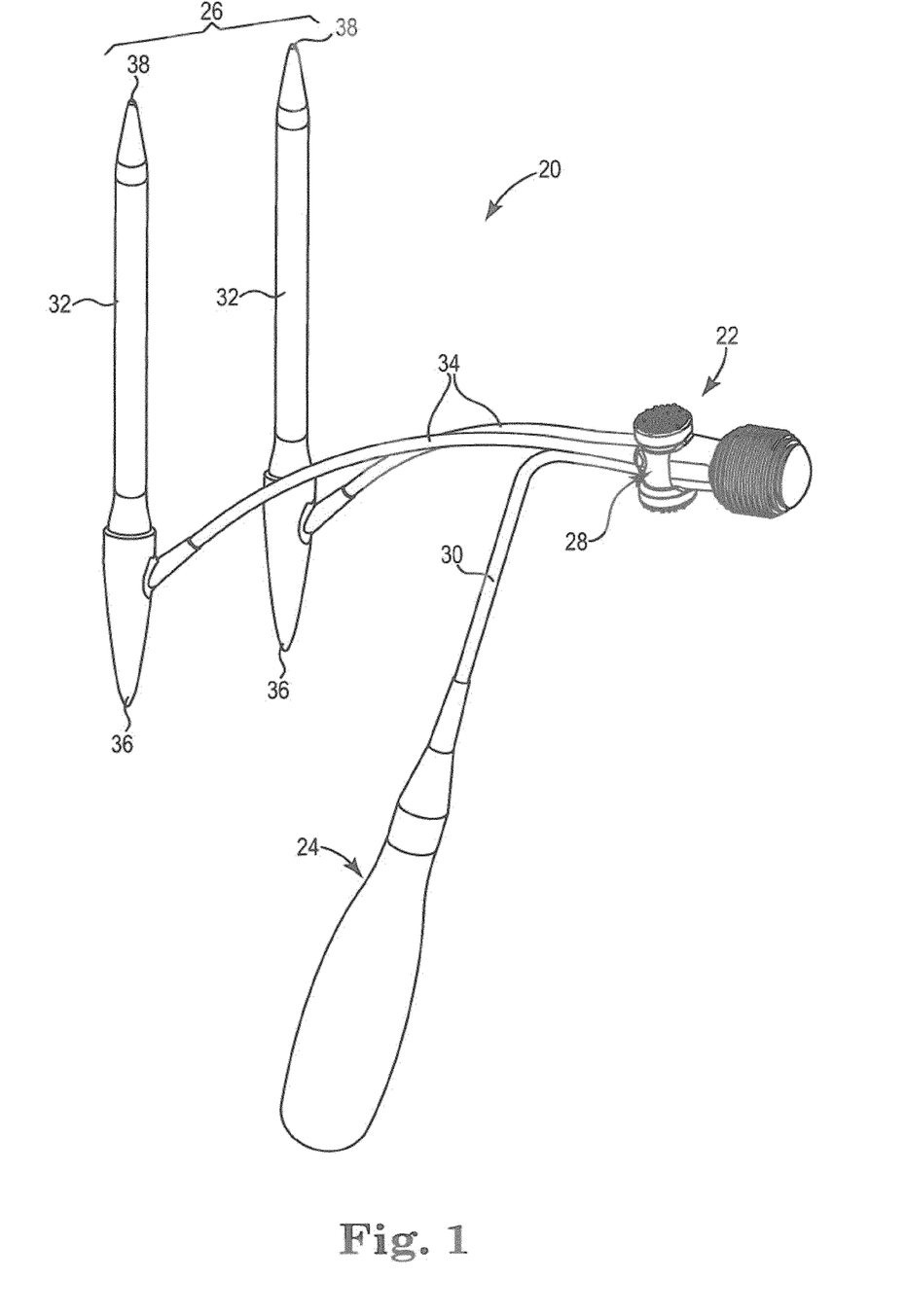
FIG. 1 is a perspective view of one embodiment of a body implantable penile prosthetic assembly including a pump connected to a reservoir and a penile implant.

FIG. 1 is a perspective view of one embodiment of a penile prosthetic assembly 20. The penile prosthetic assembly 20 includes a pump 22 connected to a reservoir 24 and a penile implant 26, and a release mechanism 28 connected between the reservoir 24 and the penile implant 26.

Generally, the pump 22 is implanted into the scrotum of the user and includes the release mechanism 28, the reservoir 24 is implanted within the abdomen of the user, and the implant 26 is implanted within the penis. The pump 22 is operable to transfer liquid from the reservoir 24 into the penile implant 26. The penile implant 26 includes one or more bladders that contain a dilatant liquid configured to respond to shear stress, for example shear stress initiated by the flow of liquid from the reservoir 24 into the penile implant 26. The dilatant liquid hardens (exhibits increased viscosity) in the presence of shear stress to create an erection in the penile implant 26. The release mechanism 28 is operable to selectively allow the liquid pumped into the penile implant 26 to return to the reservoir 24 and thus return the penile implant 26 to a flaccid state.

The reservoir 24 is connected to the pump 22 via tubing 30, which in one embodiment is kink resistant tubing 30. The reservoir 24 contains a Newtonian liquid (i.e., a non-shear-thinning liquid) such as water or saline. In one embodiment, the assembly 20 is sealed against leakage of liquids from the cylinders 32 of the implant 26 or reservoir 24 and includes a sufficient amount of liquid in the reservoir 24 to activate the dilatant liquid in the implant 26 without undesirably accessing the assembly 20 after implantation to inject more liquid.

The reservoir 24 is sized to hold a volume of liquid between about 50-350 ml. In one embodiment, the reservoir 24 is provided as a substantially cylindrical reservoir formed from an elastic, flexible polymer with a wall thickness of between 0.010-0.060 inches. In one embodiment, the reservoir 24 is provided as a "cloverleaf" style of reservoir having multiple leaves that may be folded one against the other to compactly fold the reservoir 24 for implantation into the abdomen of the user.

Figure 4:
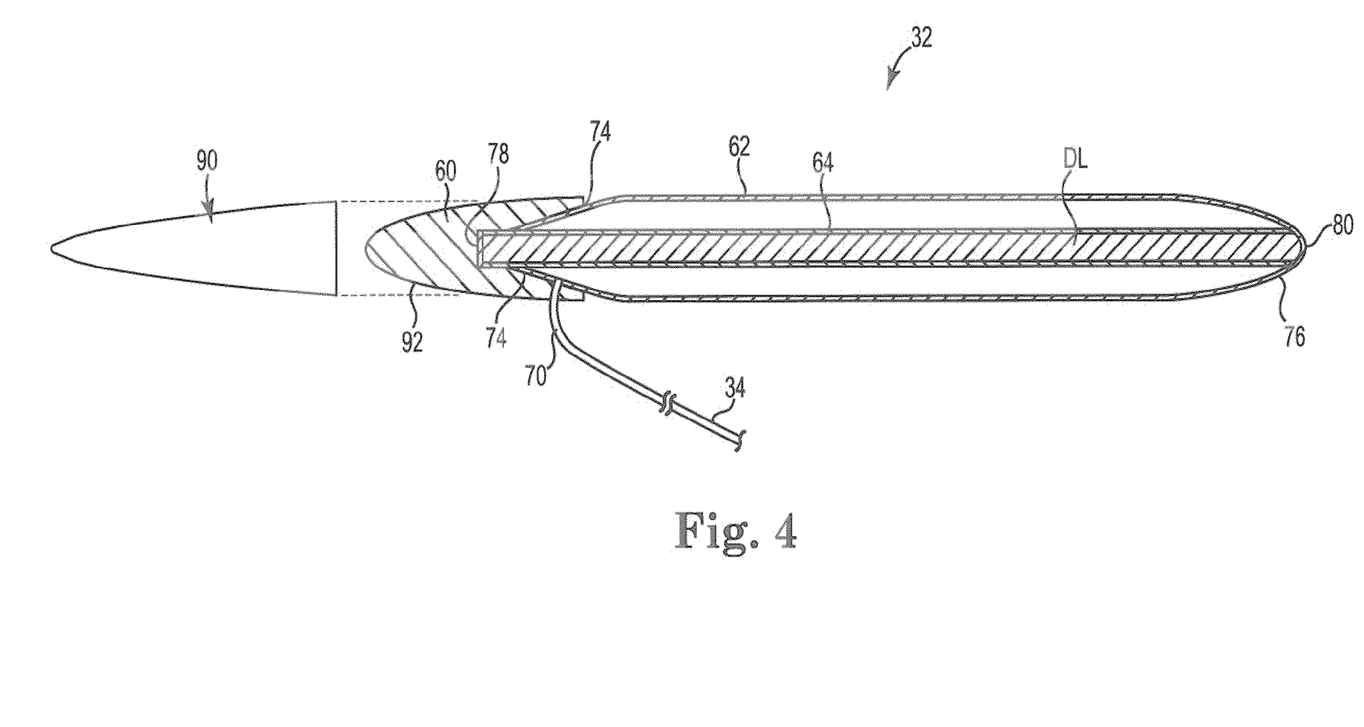
FIG. 4 is a cross-sectional view of one embodiment of the penile implant illustrated in FIG. 1 showing a bladder containing a dilatant liquid.

In one embodiment, the cylinders 32 of the penile implant 26 each contain a volume of dilatant liquid of between 50-70 mL and the reservoir 24 is a liquid-sparing reservoir that is sized to contain a volume of about 70 mL. In one embodiment, the first bladder 62 and the second bladder 64 combine to contain an erection volume of liquid (dilatant liquid plus saline) and the reservoir 24 is a fluid-sparing reservoir sized to contain at most 75% of the erection volume of liquid. In one embodiment, the first bladder 62 and the second bladder 64 combine to contain an erection volume of liquid and the reservoir 24 is a fluid-sparing reservoir sized to contain at most 50% of the erection volume of liquid. Configuring the reservoir 24 as a liquid-sparing reservoir that contains approximately half of the erection volume of the implant allows the reservoir 24 to be smaller and more comfortably implanted in the patient, whether in the abdominal area or other suitable areas. Suitable reservoirs are available from Coloplast Corp., Minneapolis, Minn.

In one embodiment, the penile implant 26 includes a pair of inflatable cylinders 32 that are sized to be implanted into the penis. Each of the cylinders 32 includes at least one bladder containing dilatant liquid and at least one bladder that is connected to the pump 22 by a tube 34. Each of the cylinders 32 includes a proximal end 36 opposite a distal end 38. During implantation, the proximal end 36 (also called a rear tip) is implanted toward the crus of the penis and the distal end 38 is implanted within the glans penis. The cylinders 32 are fabricated from material configured to collapse and be flexible when the cylinders 32 are deflated to provide the penis with a flaccid state and expand when the cylinders 32 are hardened to provide the penis with an erection. Suitable material for fabricating the cylinders 32 includes silicone, polymers such as urethanes, blends of polymers with urethane, copolymers of urethane, or the like. Suitable cylinders are available from Coloplast Corp., Minneapolis, Minn.

Figure 2:
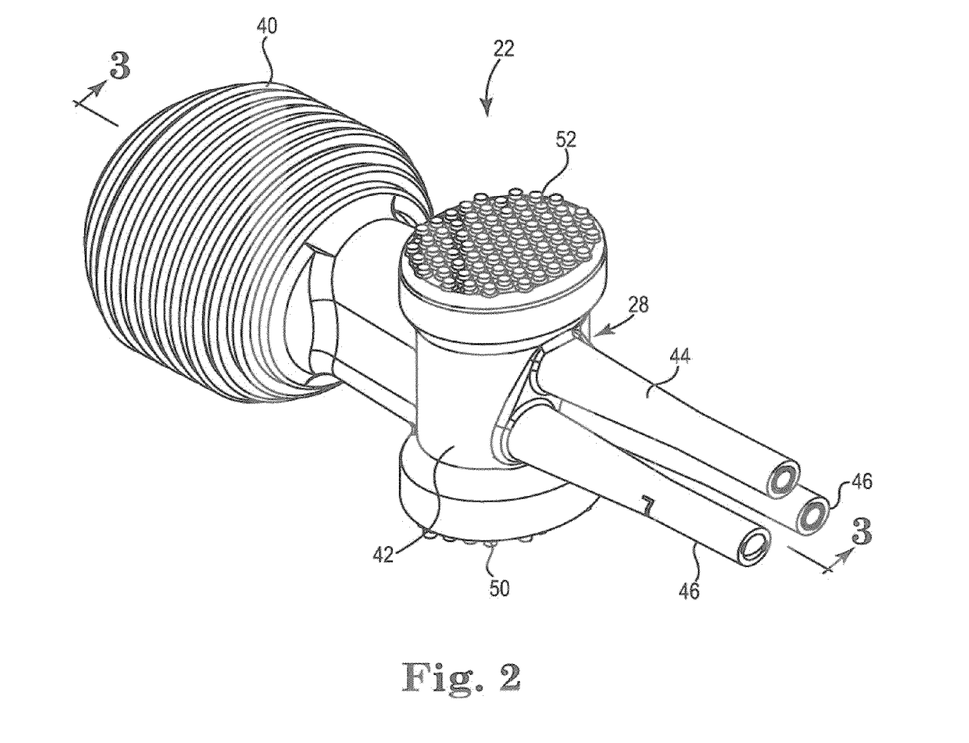
FIG. 2 is a perspective view of the pump illustrated in FIG. 1.
Figure 3:
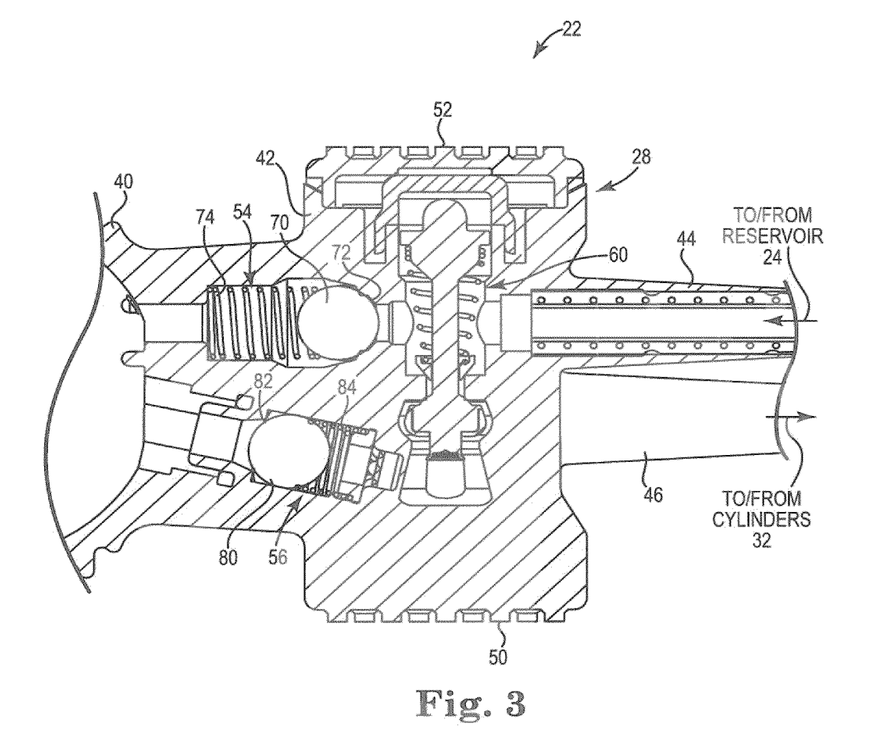
FIG. 3 is a cross-sectional view of the pump illustrated in FIG. 2.

FIG. 2 is a perspective view of the pump 22. The pump 22 includes a pump bulb 40 connected to a pump body 42 that houses the release mechanism 28 (FIG. 3). The pump body 42 has a pair of inflation ports 46 that connect with the cylinders 32 via the tubes 34 (FIG. 1), and an exhaust port 44 that connects with the reservoir 24 via the tube 30. The pump 22 is fabricated from material suitable for body implantation, such as silicone or the urethane-based materials described above for the cylinders 32 or the reservoir 24.

In one embodiment, the release mechanism 28 is integrated within the pump body 42. The pump body 42 is deformable and includes a first touch pad 50 opposite a second touch pad 52. The touch pads 50, 52 may have a circular shape or a non-circular (e.g., elliptical) shape, and other shapes for the touch pads 50, 52 are also acceptable. The pump body 42 houses or maintains valves (described below) that are activated/deactivated by pressing one or both of the touch pads 50, 52. In one embodiment, the pads 50, 52 are configured for one-touch deformation of the pump body 42 such that finger pressure applied to one of the pads 50, 52 by the implant user deforms the pump body 42 to allow liquid to flow around one or more of the internal valves and back to the reservoir 24 for rapid deflation of the cylinders 32.

In one embodiment, the pump bulb 40 is flexible and includes a pleated accordion structure that allows the pump bulb 40 to collapse and recover. The pump bulb 40 is operable to draw liquid from the reservoir 24 and transfer the liquid into the cylinders 32 (FIG. 1).

FIG. 3 is a cross-sectional view of the pump 22. The pump 22 includes an inlet valve 54 disposed within the pump body 42 that communicates between the reservoir 24 and the pump bulb 40, an exhaust valve 56 disposed within the pump body 42 that communicates between the pump bulb 40 and the cylinders 32, and an anti-autoinflation (AAI) valve 60 disposed in the pump bulb 42 transversely between the inlet valve 54 and the exhaust valve 56.

The inlet valve 54 includes a ball 70 that is biased into contact with a surface 72 by a spring 74. The ball 70 is configured to be displaced from the surface 72 (thus compressing the spring 74) when liquid flows from the reservoir 24 through the inlet tube 44 and into the pump bulb 40. When the liquid flow from the reservoir 24 is reduced, or more specifically, when the pressure driving the liquid flow from the reservoir 24 is reduced, the spring 74 biases the ball 70 into contact with the surface 72 to seat the ball on the surface 72 and block backflow of the liquid from the bulb 40 back to the reservoir 24. In this manner, the inlet valve 54 is provided as a one-way inlet valve that allows liquid to flow from the reservoir 24 to fill the bulb 40.

The exhaust valve 56 includes a ball 80 that is biased into contact with a surface 82 by a spring 84. The ball 80 is configured to be displaced from the surface 82 (thus compressing the spring 84) when liquid flows from the pump bulb 40 through the exhaust valve 56 toward the cylinders 32. For example, compressing the pump bulb 40 ejects liquid from the pump bulb 40, which unseats the ball 80 from the surface 82 to allow the liquid to flow past the ball 80 and the AAI valve 60 into the cylinders 32. Pumping the bulb 40 thus draws liquid from the reservoir 24, past the ball 80, into the bulb 40, and ejects the liquid into the cylinders 32 (FIG. 1). The spring 84 biases the ball 80 into contact with the surface 82 to block backflow of liquid from the cylinders 32 into the pump bulb 40. In this manner, the exhaust valve 56 is provided as a one-way exhaust valve.

Figure 5:
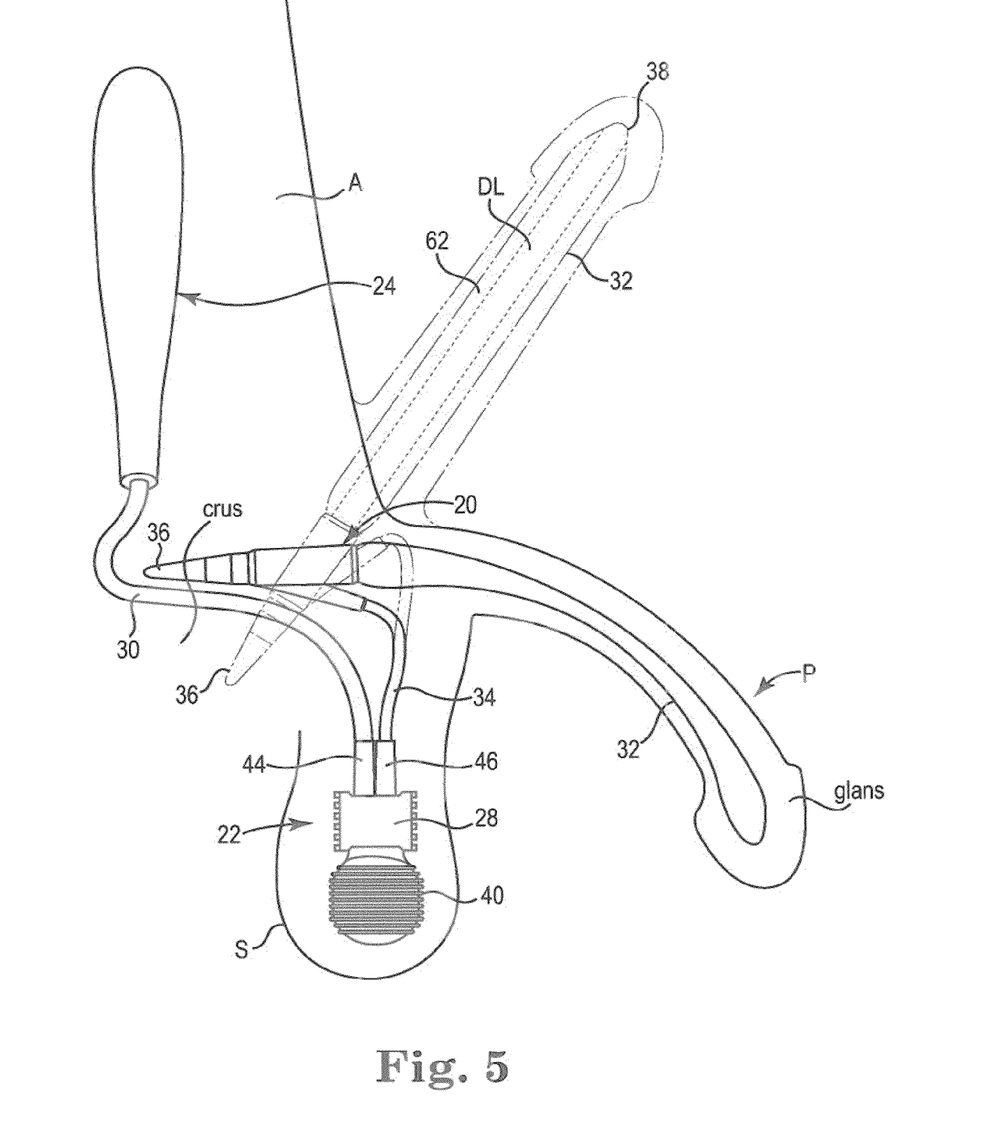
FIG. 5 is a schematic view of the body implantable penile prosthetic assembly illustrated in FIG. 1 implanted in a patient.

In one embodiment, the pump body 42 is an elastomeric chamber molded around the AAI valve 60. The AAI valve 60 is configured to allow liquid to flow from the reservoir 24 into the pump bulb 40 and out the pump bulb 40 into the cylinders 32 during inflation of the bladder 62 (FIGS. 4 and 5). The AAI valve 60 is also configured to allow for the rapid deflation of the bladders 62 in the cylinders 32. For example, in one embodiment pressing on the activation surface 52 positions the AAI valve 60 to allow fluid to flow from the bladders 62 through the pump body 42, bypassing the pump bulb 40, and flowing directly back into the reservoir 24. In addition, the AAI valve 60 is configured to prevent undesirable autoinflation of the cylinders 32 by preventing fluid from flowing from the reservoir 24 directly into the bladders 62 (i.e., undesirably bypassing the pump bulb 40).

FIG. 4 is a cross-sectional side view of one embodiment of a cylinder 32 of the penile implant 26. One cylinder 32 of the penile implants 26 is described with the understanding that the typical application would include two implanted cylinders 32, one in each of the two corpora cavernosa of the patient. The penile implant 26 is substantially cylindrical or otherwise suited to be implantable into a corpora cavernosum of the penis.

The penile implant 26 includes a proximal tip 60, a first bladder 62 connected to the proximal tip 60 and communicating with the reservoir 24 via a conduit 70 that connects with the tubing 34, and a second bladder 64 containing dilatant liquid DL that is disposed inside of the first bladder 62. Suitable dilatant liquids DL include oobleck (a solution of corn starch and water), a suspension of silica in water, or a solution of polyvinyl acetate/borax/water. One suitable oobleck solution is 2 parts corn starch in 1 part water that forms a non-Newtonian solution that is configured to become thicker/harden in a nearly instantaneous manner when shear stress is applied to the oobleck solution.

The penile implant 26 is illustrated with the first bladder 62 displaced a distance away from the second bladder 64 for improved descriptive clarity, although it is to be understood that a flaccid implant 26 (e.g., with the dilatant liquid not activated by shear) would have the bladder 62 relaxed in a wrinkled or crumpled state where the bladder 62 might even contact the second bladder 64. In one embodiment, the first bladder 62 and the second bladder 64 are arranged in a coaxial manner with the first bladder 62 disposed around the second bladder 64 of the penile implant 26. In one embodiment, the first bladder 62 and the second bladder 64 are arranged in a coaxial manner with the second bladder 64 disposed around the first bladder 62. In one embodiment, the first bladder 62 and the second bladder 64 are arranged in a side-by-side orientation.

The proximal tip 60 is a substantially solid proximal tip that is formed to receive the bladders 62, 64. The first bladder 62 extends from a proximal end of 74 that is connected to the proximal tip 60 to a distal closed end 76. In one embodiment, the first bladder 62 is provided as a sealed and substantially enclosed bladder, and the second bladder 64 is disposed inside of the first bladder 62. The second bladder 64 extends between a proximal end 78 that is connected with the proximal tip 60 and a closed distal end 80.

In one embodiment, an optional rear tip extender 90 is provided that is attachable to a proximal end portion 92 of the proximal tip 60. The overall length of a penis includes an internal body portion located at a proximal end (termed the crus of the penis) to an external distal end (termed the glans penis). Naturally, the length of the penis differs between patients. The optional rear tip extender 90 is provided to extend the penile implant 26 a greater distance in the proximal direction, which allows the penile prosthetic to extend into the crus of the penis for an improved fit.

Suitable materials for fabricating the penile implant 26 include polymers, with two examples being polyurethane or silicone. For example, in one embodiment the bladder 62 is fabricated from a urethane material sold under the trademark BIOFLEX available from Coloplast Corp., Minneapolis, Minn. and the distal end 76 of the bladder 62 is subsequently dipped in additional urethane material that cures to provide a desirable leading-end shape to the bladder 62. In one embodiment, the bladder 62 is formed from silicone, which is dissimilar to urethane. To facilitate the attachment of these two dissimilar materials, in one embodiment the silicone bladder is coated with fumed silica to prepare the surface for bonding with a urethane distal end tip.

FIG. 5 is a schematic side view of the penile prosthetic assembly 20 implanted in a user. The cylinders 32 are implanted in the penis P with the proximal end 36 inserted near the crus and the distal end 38 implanted within the glans. The smaller, liquid-sparing reservoir 24 is implanted within the abdomen A and the pump 22 is implanted within the scrotum S. The penile prosthetic assembly 20 is operable consistent with the description above to transfer liquid from the reservoir 24 into the first letter 62 to impart a shear on the dilatant liquid in the bladder 64, thus hardening the penile implant 26 to create an erection.

In one exemplary implantation approach, the groin area of the patient is cleaned, shaved, and suitably prepped with, for example, a surgical solution prior to draping with a sterile drape. A retraction device, such as a retractor sold under the trademark LONE STAR available from Lone Star Medical Products of Stafford, Tex., is placed around the penis. Thereafter, the surgeon forms an incision to access the corpora cavernosum of the patient, where suitable examples of incisions include either an infrapubic incision or a transverse scrotal incision.

The infrapubic incision is initiated between the umbilicus and the penis (i.e., above the penis), whereas the transverse scrotal incision is made across an upper portion of the patient's scrotum. As an example of the transverse scrotal approach, the surgeon forms a 2-3 cm transverse incision through the subcutaneous tissue of the median raphe of the upper scrotum and dissects down through the Dartos fascia and Buck's fascia to expose the tunicae albuginea of the penis.

Thereafter, each corpora cavernosum is exposed in a corporotomy where a small (approximately 1.5 cm) incision is formed to allow the surgeon to access and dilate the corpora cavernosum. The corpora cavernosum is dilated distally toward the glans and proximally toward the crus with a suitable tool to create a space for the penile implant 26. For example, the surgeon begins dilation of both the distal and proximal corpora cavernosum by introducing an 8 mm dilator into the spongy tissue of the corpora with sequential progression to about a 14 mm dilator, each of which are introduced and pushed distally toward the glans penis and proximally toward the crus of the penis. The surgeon measures a length of the dilated corpora cavernosum to facilitate selection of the proper length of the penile implant 26 and adjusts the length of the implant by adding an appropriately sized rear tip extender 90 (FIG. 4) as desired.

After dilation of the corpora cavernosa, a deflated penile implant 26 (FIG. 4) is inserted into the prepared corporotomy. The surgeon may palpate the end of penis at the subcoronal area to locate the distal end 80 of the penile implant 26 to ensure proper interior placement of the prosthesis in the patient.

The reservoir 24 is connected to the penile implant 26 via the tubing 30 (FIG. 1) and the surgeon inflates the bladder 62 with liquid from the reservoir 24 to shear thicken the dilatant liquid DL in the second bladder 64 to ensure proper function of the system 20. Thereafter, the liquid-sparing reservoir 24 is filled with an appropriate volume of liquid and implanted into the abdomen, for example in the space of Retzius, and the surgical site is closed to allow the patient to heal.

The pump 22 is operable to transfer liquid from the reservoir 24 into the first bladder 62. Filling the first bladder 62 with liquid creates a shear stress on the second bladder 64 containing the dilatant liquid DL, and the dilatant liquid DL responds by shear thickening to a hardened state. Once the first bladder 62 is pressurized, the shear (i.e., force per unit area) of the pressurized liquid in the first bladder 62 will impose a substantially constant shear on the dilatant liquid DL in the second bladder 64, which will increase the viscosity in the dilatant liquid DL and harden the penile implant 26. That is to say, the shear applied to the dilatant liquid can be constant such that the rate of shear applied to the dilatant liquid is zero and the implant 26 will maintain the erect, hardened state.

In one embodiment, the pump 22 transfers saline solution from the reservoir 24 into the first bladder 62 such that the pump 22 transfers approximately half of an erection volume of liquid from the reservoir 24 into the implant 26 and yet fully inflates the implant 26 to an erect state.

In one embodiment, a method treating erectile dysfunction includes implanting a penile implant 26 including a first bladder 62 and a second bladder 64, the second bladder 64 filled with a liquid having a rest viscosity; increasing a pressure in the first bladder 62 of the penile implant 26 from a first pressure to a second pressure; increasing a viscosity in the liquid from the rest viscosity to a second viscosity greater than the rest viscosity; and maintaining the first bladder 62 of the penile implant 26 at the second pressure and the liquid in the second bladder 64 at the second viscosity. For example, in one embodiment the pressure and the first bladder 62 is increased from about zero PSIG to a second pressure of about 15 psi and the viscosity of the dilatant liquid increases by at least an order of magnitude to provide the implant 26 with a column strength of about 4-15 pounds force.

FIGS. 6-11 illustrate embodiments that provide an implantable penile implant that is configured as a peristaltic pump configured to transfer liquid from an implanted reservoir into a first bladder of the penile implant, which imparts a shear stress to a dilatant liquid stored in a second bladder of the penile implant, thus causing the dilatant liquid to shear harden and creating an erection in the implant.

Peristaltic means a wavelike contraction of a tube or a tubular structure between an entrance opening and an exit opening by which contents in the tube are forced to the exit opening. Peristaltic compression is a wavelike contraction that is provided, in one example, by pinching the tube with fingers (or a device) and sliding the fingers/device from near the entrance opening toward the exit opening. Peristaltic compression is referred to as a moving compression.

Figure 6:
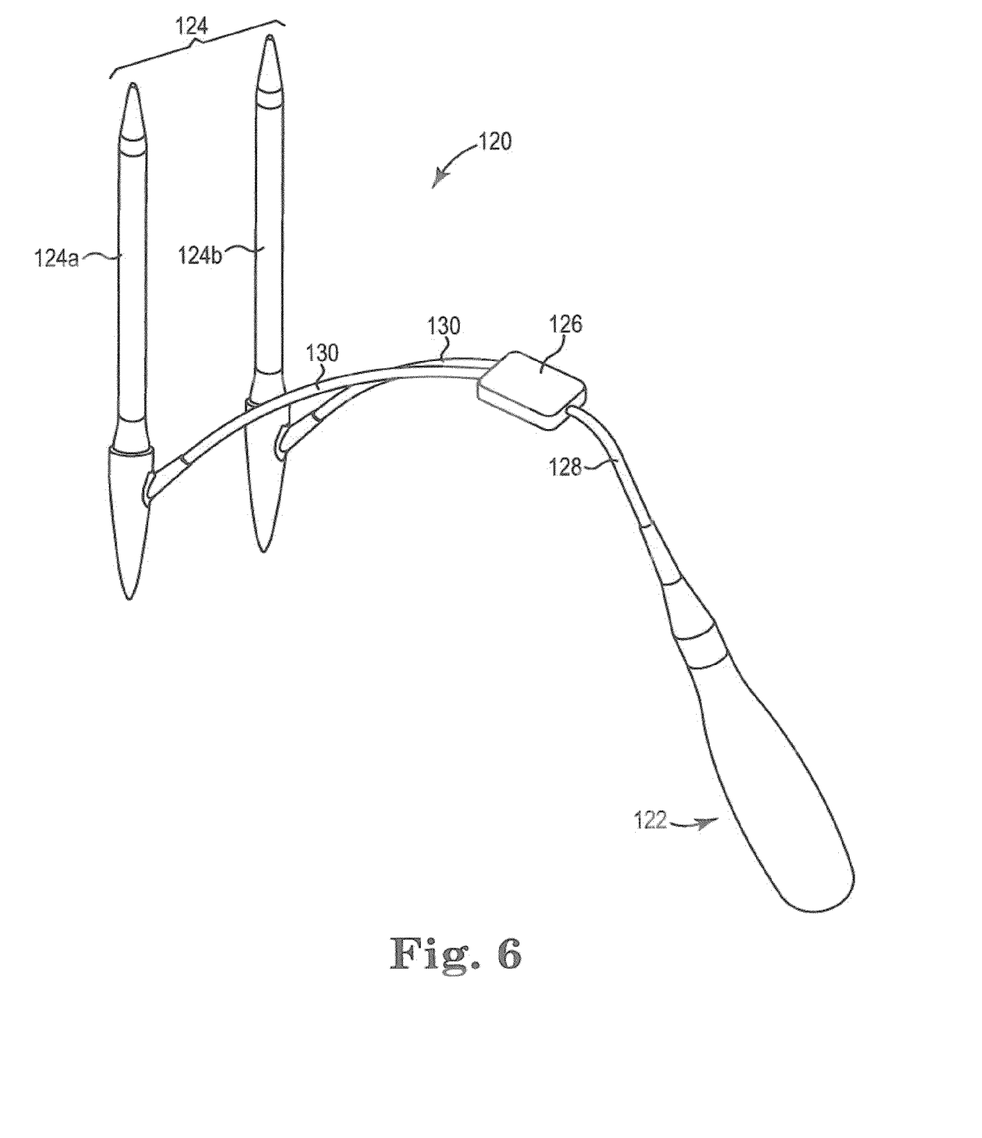
FIG. 6 is a perspective view of one embodiment of a body implantable penile prosthetic assembly including a reservoir coupled to a penile implant.

FIG. 6 is a perspective view of one embodiment of a penile prosthetic system 120. The penile prosthetic system 120 (system 120) includes a fluid reservoir 122, a pair of penile prosthetic pumps 124, and a check valve 126 connected between the fluid reservoir 122 and the penile prosthetic pumps 124. In one embodiment, the penile prosthetic pumps 124 includes a first prosthetic pump 124a that is implantable into a first corpora cavernosum of the penis and a second prosthetic pump 124b that is implantable into a second corpora cavernosum of the penis. The reservoir 122 is implantable in the body, for example within the abdomen of the user. Tubing 128 is connected between the fluid reservoir 122 and the check valve 126, and each of the prosthetic pumps 124 includes tubing 130 connected to the check valve 126. Thus, the pumps 124 communicate with the reservoir 122 via the tubing 128, 130.

Figure 7A:
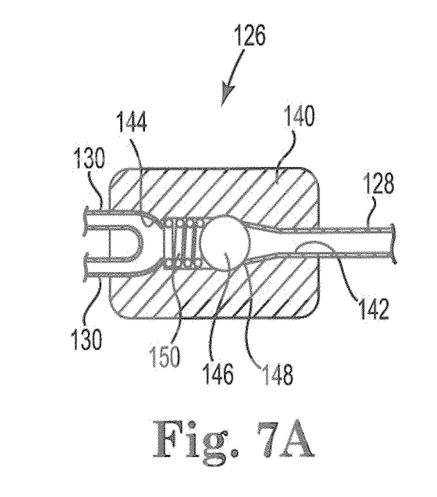
FIG. 7A is a top cross-sectional view and FIGS. 7B-7C are side cross-sectional views of a valve mechanism located between the reservoir and the penile implant illustrated in FIG. 6.

FIG. 7A is a cross-sectional top view of one embodiment of the check valve 126. The check valve 126 includes a body 140, an inlet opening 142 and an outlet opening 144, and a ball 146 that is biased against a seat 148 by a spring 150. In one embodiment, the body 140 is a deformable body molded or otherwise fabricated from a resilient/compressible polymer such as silicone or a thermoplastic polymer.

Figure 7B:
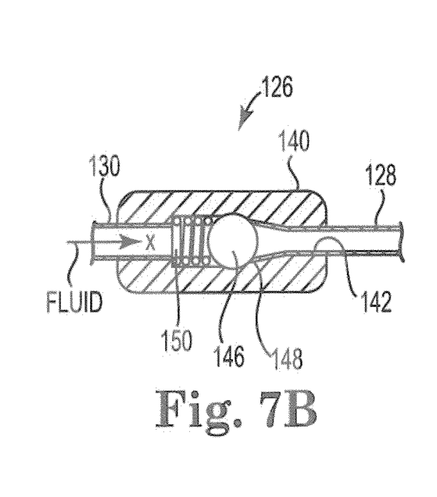

The check valve 126 is configured to allow fluid to be drawn from the reservoir 122 (FIG. 6) into the pumps 124 and impede or restrict the fluid from flowing out of the pumps 124 and back to the reservoir 122 until this flow condition is selectively permitted by the user (as illustrated in FIG. 7B).

During an exemplary inflation of the pumps 124, the fluid is moved through the tubing 128 and the inlet opening 142 by a pumping condition or a pressure condition that moves the fluid out of the reservoir 122 with a pressure sufficient to displace the ball 146 off of the seat 148. The fluid moves through the outlet opening 144 and the tubing 130 and into the penile prosthetic pumps 124 (FIG. 6).

FIG. 7B is a cross-sectional side view of the check valve 126 illustrating that the fluid inside of the penile prosthetic pumps 124 is prevented from flowing back through the check valve 126 by the spring 150 that biases the ball 146 against the seat 148. In this manner, the fluid employed to inflate the pumps 124 (FIG. 6) maintains the pumps 124 in the inflated state until the user selectively manipulates the check valve 126 to allow deflation of the pumps 124.

Figure 7C:
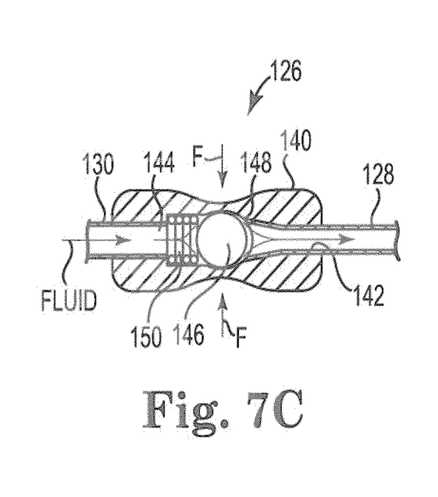

FIG. 7C is a cross-sectional side view of the check valve 126 illustrating user-manipulation of the check valve 126 to allow deflation of the pumps 124. In one embodiment, the user-manipulation of the check valve 126 includes an application of a force F to deform the body 140. Deformation of the body 140 results in the ball 146 being displaced off of the seat 148, which allows the fluid to flow from the outlet opening 144 past the ball 146 and back through the inlet opening 142 to the reservoir 122 (FIG. 6).

Figure 8:
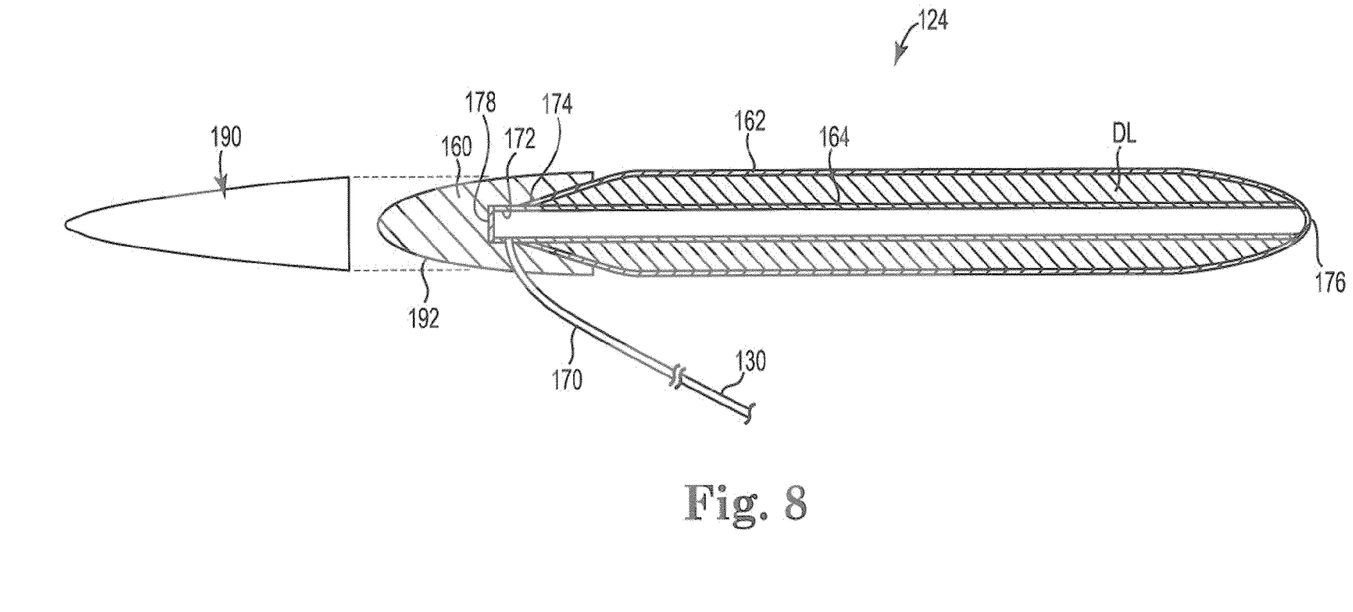
FIG. 8 is a cross-sectional view of one embodiment of the penile implant illustrated in FIG. 6 showing a bladder containing a dilatant liquid and disposed around a peristaltic pump/bladder.

FIG. 8 is a cross-sectional side view of one embodiment of the penile prosthetic pump 124. One of the penile prosthetic pumps 124 is described with the understanding that the typical application would include two implanted pumps 124, one in each of the two corpora cavernosa of the patient.

The penile prosthetic pump 124 includes a proximal tip 160, a first bladder 162 connected to the proximal tip 160, and a peristaltic bladder 164 (or peristaltic tubing 164) disposed inside of the first bladder 162.

A conduit 170 is formed to provide a fluid communication path between the reservoir 122 (FIG. 6) and the peristaltic bladder 164. In one embodiment, the proximal tip 160 is a substantially solid proximal tip that is formed to provide a chamber 172, with the conduit 170 extending from the chamber 172 to the reservoir 122 and the peristaltic tubing 164 communicating with and extending from the chamber 172.

The first bladder 162 extends from a proximal end 174 that is connected to the proximal tip 160 to a closed distal end 176. In one embodiment, the first bladder 162 is sealed to contain a dilatant liquid DL and the peristaltic tubing 164 is disposed inside of the first bladder 162.

The peristaltic tubing 164 has a proximal end 178 that is connected to the proximal tip 160 and extends to the closed distal end 176. Peristaltic compression applied from the proximal end 178 toward the distal end 176 of the peristaltic tubing 164 pumps fluid from the reservoir 122 (FIG. 6) into the second bladder or tubing 164 and imparts a shear stress (e.g., pressurizes) the dilatant liquid DL in the first bladder 162.

In one embodiment, an optional rear tip extender 190 is provided that is attachable to a proximal end portion 192 of the proximal tip 160 to extend the penile prosthetic pump 124 a greater distance in the proximal direction, which allows the penile prosthetic to extend into the crus of the penis for an improved fit.

Suitable materials for fabricating the penile prosthetic pump 124 include polyurethane or silicone similar to the implant 26 described above.

Figure 9:
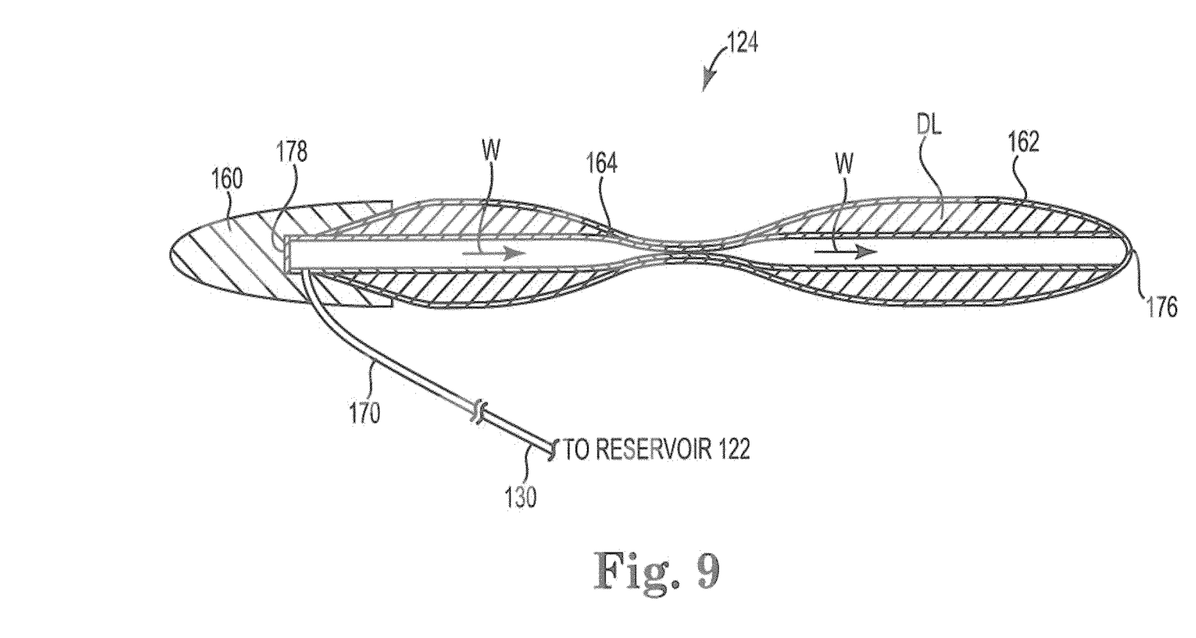
FIG. 9 is a cross-sectional side view of the penile implant illustrated in FIG. 8 peristaltically compressed to draw fluid from the reservoir into the peristaltic pump/bladder.

FIG. 9 is a cross-sectional side view of the pump 124 peristaltically compressed to draw fluid from the reservoir 122 into the tubing/bladder 164 to stress the dilatant liquid DL in the bladder 162, which causes the dilatant liquid to shear thicken to a hardened state to form an erection in the penile prosthetic pump 124. In one embodiment, the user compresses the tubing/bladder 164 by squeezing the walls of the peristaltic tubing 164 together, and while squeezing the walls of the peristaltic tubing 164, slides the compression from the proximal end 178 toward the distal end 176 of the tubing 164. The moving compression of the peristaltic wave W suctions the fluid from the reservoir 122, through the conduit 170, and increases the pressure of the fluid in the peristaltic tubing 164, which imparts a shear on the dilatant liquid in the bladder 162. Subsequent, repeated moving compressions of the peristaltic wave W will drive more fluid into the tubing/bladder 164, which further increases the pressure in the tubing/bladder 164 to ensure that the dilatant liquid in the bladder 162 is maintained in the hardened state.

Figure 10:
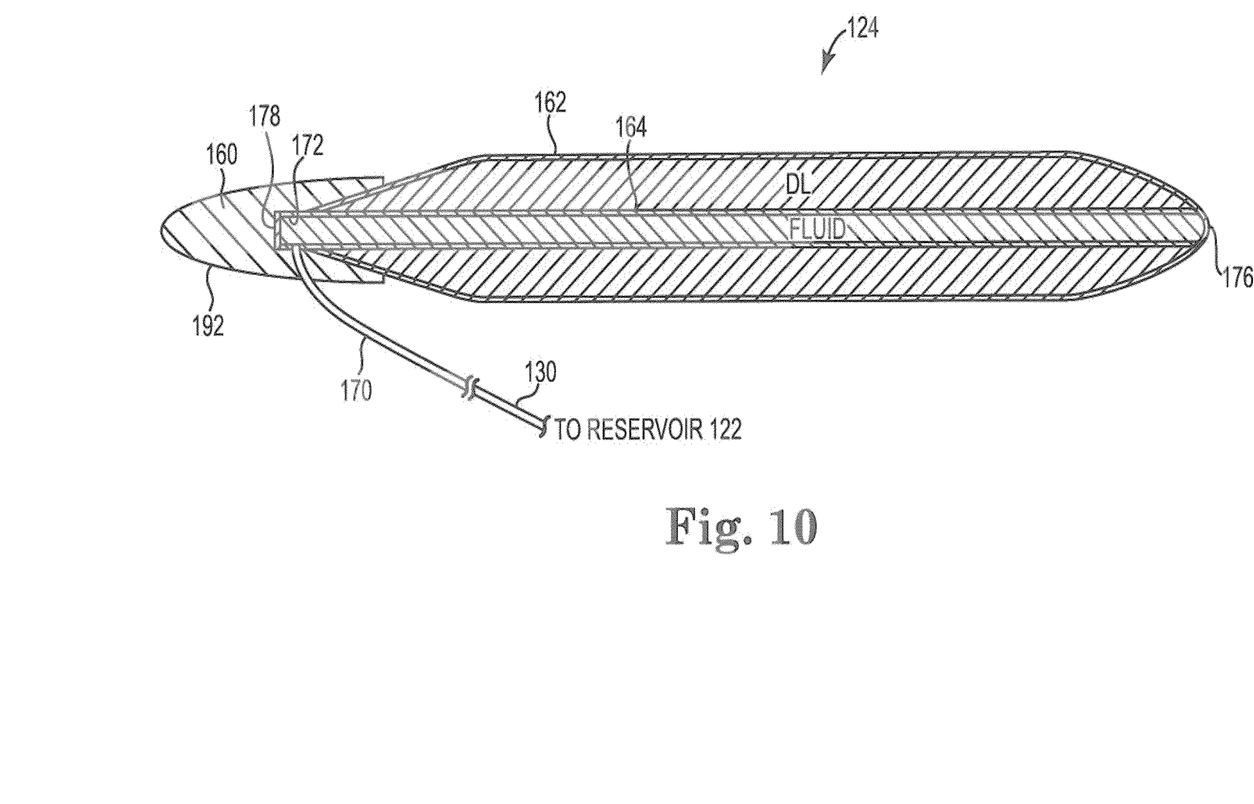
FIG. 10 is a cross-sectional side view of the penile implant illustrated in FIG. 9 after peristaltic activation has hardened the dilatant liquid causing the implant to become erect.

FIG. 10 is a cross-sectional side view of the penile prosthetic pump 124 showing the fluid been peristaltically pumped from the reservoir 122 into the peristaltic tubing 164 and imparting a stress onto the dilatant liquid DL in the first bladder 162. The check valve 126 (FIG. 7B) impedes the flow of the fluid out of the peristaltic tubing 164, which allows the penile prosthetic pump 124 to maintain the inflation pressure/stress against the dilatant liquid until the bladder 162 and thus maintain the erection. The user may selectively activate the check valve 26 to drain the fluid L from the tubing 164 back into the reservoir 24 to relieve the stress on the dilatant liquid in the bladder 162 and return the implant 124 to a flaccid state.

Figure 11:
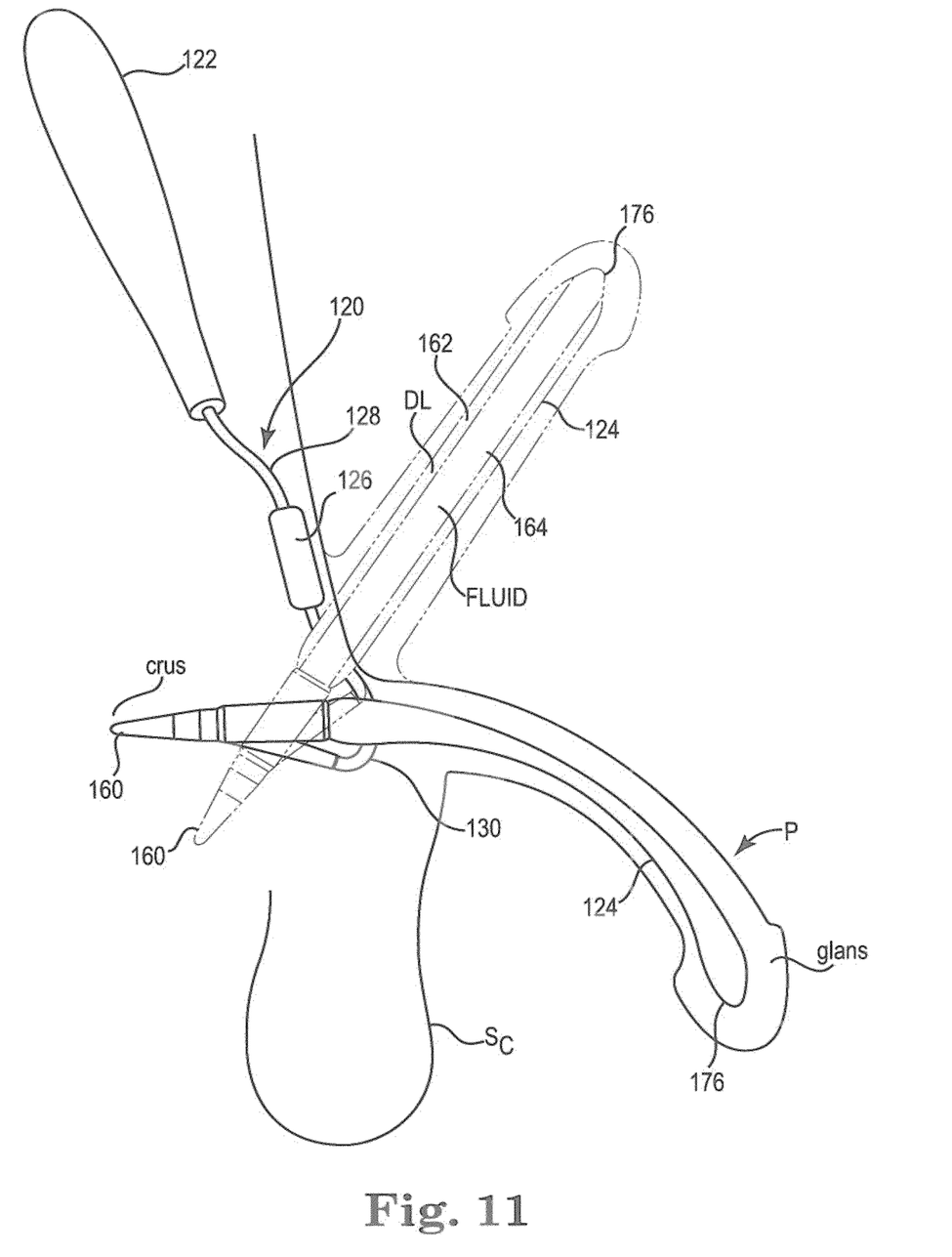
FIG. 11 is a schematic view of the body implantable penile prosthetic assembly illustrated in FIG. 6 implanted in a patient.

FIG. 11 is a schematic view of the penile prosthetic system 120 with the reservoir 122 implanted in the patient's abdomen and a prosthetic pump 124 implanted into each corpora cavernosum of the penis P.

The peristaltic tubing/bladder 164 is illustrated as being co-axially located inside the first bladder 162 containing the dilatant liquid. Alternatively, embodiments provide for the first bladder 162 containing the dilatant liquid to be co-axially enclosed inside the peristaltic tubing/bladder 164 similar to the structure described above for the implant 26.

Embodiments described above provide a body implantable penile prosthetic assembly provide means for transferring a second liquid into a first bladder of a penile implant, imposing a shear on a dilatant liquid in the second bladder of the penile implant, and increasing a viscosity in the dilatant liquid. Embodiments described above provide a body implantable penile prosthetic assembly provide means for increasing a pressure in the first bladder of the penile implant from a first pressure to a second pressure and increasing a viscosity in the liquid from the rest viscosity to a second viscosity greater than the rest viscosity, and maintaining the first bladder of the penile implant at the second pressure and the liquid in the second bladder at the second viscosity.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of medical devices as discussed herein. Therefore, it is intended that this invention be limited only by the claims and the equivalents thereof.

What is claimed is:

1. A penile prosthetic assembly comprising:
 a penile implant including a first bladder and a second bladder, the second bladder containing a dilatant liquid, and the first bladder and a second bladder configured to combine to contain an erection volume of liquid; and
 a reservoir connectable with the penile implant;
 wherein the reservoir is configured as a fluid sparing reservoir that is sized to contain at most 50% of the erection volume of liquid; and
 means for transferring liquid from the reservoir into the first bladder of the penile implant.

2. The assembly of claim 1, wherein the reservoir is operable to transfer liquid contained in the reservoir into the first bladder of the penile implant to impose a shear on the dilatant liquid in the second bladder of the penile implant.

3. The assembly of claim 2, wherein the liquid transferred from the reservoir into the first bladder of the penile implant imposes a substantially constant shear on the dilatant liquid in the second bladder of the penile implant to increase the viscosity in the dilatant liquid and harden the penile implant.

4. The assembly of claim 1, wherein the first bladder and the second bladder of the penile implant are coaxial one relative to an other.

5. The assembly of claim 1, wherein the first bladder is disposed around the second bladder of the penile implant.

* * * * *